(12) United States Patent
Timms et al.

(10) Patent No.: US 7,662,566 B2
(45) Date of Patent: Feb. 16, 2010

(54) GENE COPY NUMBER PROFILING

(75) Inventors: Kirsten Timms, Salt Lake City, UT (US); Alexander Gutin, Salt Lake City, UT (US); Victor Abkevich, Salt Lake City, UT (US); Jerry Lanchbury, Salt Lake City, UT (US); Julie A. DeLoia, Washington, DC (US); Alfred Guirguis, Chicago, IL (US); Esther Elishaev, Pittsburgh, PA (US)

(73) Assignee: Myriad Genetics, Inc., Salt Lake City, UT (US)

( * ) Notice: Subject to any disclaimer, the term of this patent is extended or adjusted under 35 U.S.C. 154(b) by 44 days.

(21) Appl. No.: 11/944,269

(22) Filed: Nov. 21, 2007

(65) Prior Publication Data

US 2009/0029362 A1 Jan. 29, 2009

Related U.S. Application Data

(60) Provisional application No. 60/860,667, filed on Nov. 22, 2006.

(51) Int. Cl.
*C12Q 1/68* (2006.01)
*C07H 21/00* (2006.01)
*C07H 21/02* (2006.01)
*C07H 21/04* (2006.01)

(52) U.S. Cl. .................. 435/6; 536/22.1; 536/23.1; 536/24.3

(58) Field of Classification Search ............ 435/6; 536/23.1, 24.3
See application file for complete search history.

(56) References Cited

U.S. PATENT DOCUMENTS

| | | | | |
|---|---|---|---|---|
| 6,110,673 A * | 8/2000 | Shayesteh et al. | ............ | 435/6 |
| 6,326,148 B1 * | 12/2001 | Pauletti et al. | ............ | 435/6 |
| 6,455,258 B2 * | 9/2002 | Bastian et al. | ............ | 435/6 |
| 2002/0142305 A1 * | 10/2002 | Chin et al. | ............ | 435/6 |
| 2003/0008318 A1 * | 1/2003 | Pinkel et al. | ............ | 435/6 |
| 2003/0077582 A1 * | 4/2003 | Kuo et al. | ............ | 435/6 |
| 2004/0171037 A1 * | 9/2004 | Li et al. | ............ | 435/6 |
| 2006/0194220 A1 * | 8/2006 | Reddy et al. | ............ | 435/6 |
| 2006/0257895 A1 * | 11/2006 | Pinkel et al. | ............ | 435/6 |
| 2007/0207478 A1 * | 9/2007 | Paris et al. | ............ | 435/6 |
| 2007/0254295 A1 * | 11/2007 | Harvey et al. | ............ | 435/6 |
| 2008/0269067 A1 * | 10/2008 | Semizarov et al. | ............ | 506/9 |
| 2009/0075260 A1 * | 3/2009 | Distler et al. | ............ | 435/6 |

OTHER PUBLICATIONS

Iwabuchi et al. Genetic analysis of benign, low-grade, and high-grade ovarian tumors. Cancer Research vol. 55, No. 24, pp. 6172-6180 (1995).*
Pollack et al. Genome-wide analysis of DNA copy-number changes using cDNA microarrays. Nature Genetics 23 : 41-46 (1999).*
Ramaswamy et al., Multiclass cancer diagnosis using tumor gene expression signatures. PNAS 98(6) :15149-15154 (2001).*
Rhodes et al. Large-scale meta-analysis of cancer microarray data identifies common transcriptional profiles of neoplastic transformation and progression. PNAS 101 (25) : 9309-9314(2004).*
Suehiro et al., Genetic aberrations detected by comparative genomic hybridization predict outcome in patients with endometrioid carcinoma. Genes, Chromosomes & Cancer 29 (1) : 75-82 (2000).*
Zauber et al., Ki-ras gene mutations, LOH of the APC and DCC genes, and microsatellite instability in primary colorectal carcinoma are not associated with micrometastases in pericolonic lymph nodes or with patients' survival. Journal of Clinical Pathology 57 (9) : 938-42 (Sep. 2004).*
Buffart et al., *DNA Copy Number Changes at 8q11-24 in Metastasized Colorectal Cancer*, Cell. Oncol. 27(1):57-65 (2005).

* cited by examiner

*Primary Examiner*—Ethan Whisenant
(74) *Attorney, Agent, or Firm*—Benjamin G. Jackson; Jay Z. Zhang; Myriad Genetics IP Department

(57) ABSTRACT

The invention relates to copy number profile analysis. Specifically, copy number profile analysis is used to determine whether two or more separate tumors in a single individual are derived from a common source.

7 Claims, 6 Drawing Sheets

Single shared somatic mutation defines ovarian as the primary tumor.

GENE COPY NUMBER PROFILING

CROSS-REFERENCE TO RELATED APPLICATIONS

The present application is related to and claims priority under 35 USC § 119(e) to provisional patent application Ser. No. 60/860,667, filed Nov. 22, 2006, which is incorporated herein by reference.

FIELD OF THE INVENTION

The invention relates to methods for characterizing cancer.

BACKGROUND OF THE INVENTION

A large number of cancer patients present to their physician with more than one tumor. In some instances the origin of the different tumors in the patient are distinguishable based on standard histological analysis (i.e., examination of the suspect tissue by a pathologist under the microscope). In other cases it is difficult to identify the tissue of origin of the cancer, or properly stage the cancer, if the relationship between the tumors in a patient is not properly ascertained. Are the tumors independent primaries? Are the tumors a primary and a metastasis? The answers to these questions are not always knowable based on standard clinical practice. Critical health care decisions are based on the staging and classification of cancer in a patient.

Simultaneous cancers are not uncommon with endometrial and ovarian tumors. Around 3000-4000 women, per year, present with simultaneous ovarian and endometrial tumors. The best course of treatment depends on whether the cancers are independent primary ovarian and endometrial tumors, an endometrial primary and an ovarian metastasis, or an ovarian primary and an endometrial metastasis. Simultaneous tumors of the endometrium and ovary can be difficult to unambiguously identify using standard histopathology techniques.

Head and neck cancer patients can present with two (or more) tumors: sometimes the cancers are a primary and a metastasis, and sometimes the cancers are two primaries. Two primaries may be treated surgically, whereas metastatic (disseminated) disease may be more appropriately treated with systemic therapy.

There is a need for a high-throughput, high-resolution method of determining, without a priori knowledge concerning stage or metastasis, whether two or more given tumors are independent primaries or primaries with related metastases.

BRIEF SUMMARY OF THE INVENTION

The invention relates to characterizing the gene copy number profile of two or more cancers (e.g., tumors) from an individual. The invention is useful for a number of applications including distinguishing, in patients that present clinically with two or more cancers, independent primary cancers, metasynchronous primary cancers and a primary/metastatic cancer pair. Distinguishing between a pair of independent primary cancers and a primary/metastasis pair of cancers is very important for staging the patient's cancer. Other applications, include, but are not limited to comparing the copy number profiles of two or more samples, where one of the samples is from a tumor that arose later in time (including after the first tumor has been removed or treated) to determine if the earlier and latter cancers are independent primary cancers or are related as a primary and metastasis. Critical treatment decisions are made based on accurate staging. Accurate staging can be difficult in a number of cancers based on currently used techniques.

Generally speaking, the invention relates to comparing the high resolution genomic DNA copy number profiles for two or more samples suspected of being cancerous. Comparison of the DNA copy number profiles for the two or more samples from an individual according to the methods disclosed herein allows for distinguishing or associating the two or more cancers genetically. Two cancers are associated genetically, according to the methods of the invention, when the first cancer and the second cancer are found to have a common DNA copy number profile and where one of the cancers has one or more additional lesions. Two cancers are distinguished genetically according to the methods disclosed herein if they harbor substantially different genomic DNA copy number profiles. Critical staging information and important medical decisions are based on the distinction between a primary/metastatic cancer pair and independent primary cancers.

The present invention further provides a method for determining the stage of a patient's cancer or whether two separate tumor samples are derived from the same source, comprising:

providing a first copy number profile from a first tumor sample obtained from a patient, said first copy number profile comprising copy number information for a plurality of genomic loci;

providing a second copy number profile from a second tumor sample obtained from said patient, said second copy number profile comprising copy number information for said plurality of genomic loci;

optionally providing a third copy number profile from a normal non-cancerous sample obtained from said patient, said third copy number profile comprising copy number information for said plurality of genomic loci;

comparing said first copy number profile and said second copy number profile, and optionally said third copy number profile; and communicating to a recipient the result of said comparing step, wherein if said first copy number profile is substantially similar to said second copy number profile, said recipient concludes said first tumor sample and said second tumor sample are from the same source; and wherein if said first copy number profile is substantially different from said second copy number profile, said recipient concludes said first tumor sample and said second tumor sample are from different sources.

The present invention further provides a method for determining the stage of a patient's cancer or whether two separate tumor samples are derived from the same source, comprising:

obtaining a first tumor sample from the patient to provide a first copy number profile from the first tumor sample, said first copy number profile comprising copy number information for a plurality of genomic loci;

obtaining a second tumor sample from the patient to provide a second copy number profile from the second tumor sample, said second copy number profile comprising copy number information for said plurality of genomic loci, and optionally obtaining a normal non-cancerous sample from said patient to provide a third copy number profile comprising copy number information for said plurality of genomic loci, wherein said first and second tumors are separate tumors, and wherein said first copy number profile and second copy number profile and optionally the third copy number profile are compared to determine whether the first and second profiles are substantially similar or different; and receiving the result of the comparison, wherein if said first copy number profile is substantially similar to said second copy number profile, it indicates said first tumor sample and said second tumor sample are from the same source; and wherein if said first copy number profile is substantially different from said second copy number profile, it indicates said first tumor sample and said second tumor sample are from different sources.

In one embodiment, the method for determining the stage of a patient's cancer or whether two separate tumor samples are derived from the same source, comprises:

obtaining a differential copy number profile analysis result obtained by the steps of:

providing a first copy number profile from a first tumor sample obtained from a patient, said first copy number profile comprising copy number information for a plurality of genomic loci;

providing a second copy number profile from a second tumor sample obtained from said patient, said second copy number profile comprising copy number information for said plurality of genomic loci;

optionally providing a third copy number profile from a normal non-cancerous sample obtained from said patient, said third copy number profile comprising copy number information for said plurality of genomic loci; and comparing said first copy number profile and said second copy number profile, and optionally said third copy number profile;

wherein if said first copy number profile is substantially similar to said second copy number profile, it indicates said first tumor sample and said second tumor sample are from the same source, wherein if said first copy number profile is substantially different from said second copy number profile, it indicates said first tumor sample and said second tumor sample are from different sources.

The present invention further provides a method for determining a treatment regimen for a cancer patient having at least two separate tumors. The method comprises (1) determining the stage of a patient's cancer or whether the two separate tumor samples are derived from the same source or different sources, or whether the two separate tumors are one primary and the other metastatic tumor, as described herein, and then (2) treating a patient according to the result of the determining step. Optionally, the determining step further comprises a step of determining the presence or absence of a mutation in one or more auxiliary genes as described herein.

Unless otherwise defined, all technical and scientific terms used herein have the same meaning as commonly understood by one of ordinary skill in the art to which this invention pertains. Although methods and materials similar or equivalent to those described herein can be used in the practice or testing of the present invention, suitable methods and materials are described below. In case of conflict, the present specification, including definitions, will control. In addition, the materials, methods, and examples are illustrative only and not intended to be limiting.

Other features and advantages of the invention will be apparent from the following detailed description, and from the claims.

DETAILED DESCRIPTION OF THE INVENTION

The invention relates to characterizing the gene copy number profile of two or more cancers (e.g., tumors) from an individual. The invention is useful for a number of applications including distinguishing, in a patient that presents with two or more cancers, independent primary cancers, metasynchronous primary cancers, and a primary/metastatic cancer pair. Distinguishing between a pair of independent primary cancers and a primary metastasis pair of cancers is very important for staging the patient's cancer. Critical treatment decisions are made based on accurate staging. Accurate staging can be difficult in a number of cancers based on currently used techniques.

The invention provides a method of determining whether two separate tumor samples are derived from the same source, comprising:

providing a first copy number profile from a first tumor sample obtained from a patient, said first copy number profile comprising copy number information for a plurality of genomic loci;

providing a second copy number profile from a second tumor sample obtained from said patient, said second copy number profile comprising copy number information for said plurality of genomic loci;

comparing said first copy number profile and said second copy number profile;

wherein if said first copy number profile is substantially similar to said second copy number profile, it indicates said first tumor sample and said second tumor sample are from the same source; and wherein if said first copy number profile is substantially different from said second copy number profile, it indicates said first tumor sample and said second tumor sample are from different sources.

As used herein, two tumor samples are "derived from the same source" or "derived from a common source" when they share a common cancerous progenitor. For example, when a primary tumor comprising an effectively homogenous clone of cancer cells metastasizes, a new secondary tumor is formed somewhere in the body distant from the site of the primary tumor. Since the primary tumor generally arises from a single cancerous cell and because the secondary tumor arises from the primary tumor, both tumors can be said to be "derived from the same source." "Independent primary" tumors are not derived from the same source.

As used herein, "copy number profile" means a collection of data representing the number of copies of genomic DNA at a plurality of genomic loci for a given sample. For instance, given three genomic loci of interest—A, B, and C—a copy number profile represents the number of copies of DNA for A, B and C. In this context, "genomic locus" means a location within the genome of a cell and usually encompasses a stretch of genomic DNA between two points in the genome of a cell. This stretch of genomic DNA consists of a nucleotide sequence. "Copy number" in this context means the number of times such a nucleotide sequence appears in a sample.

Figure 5:
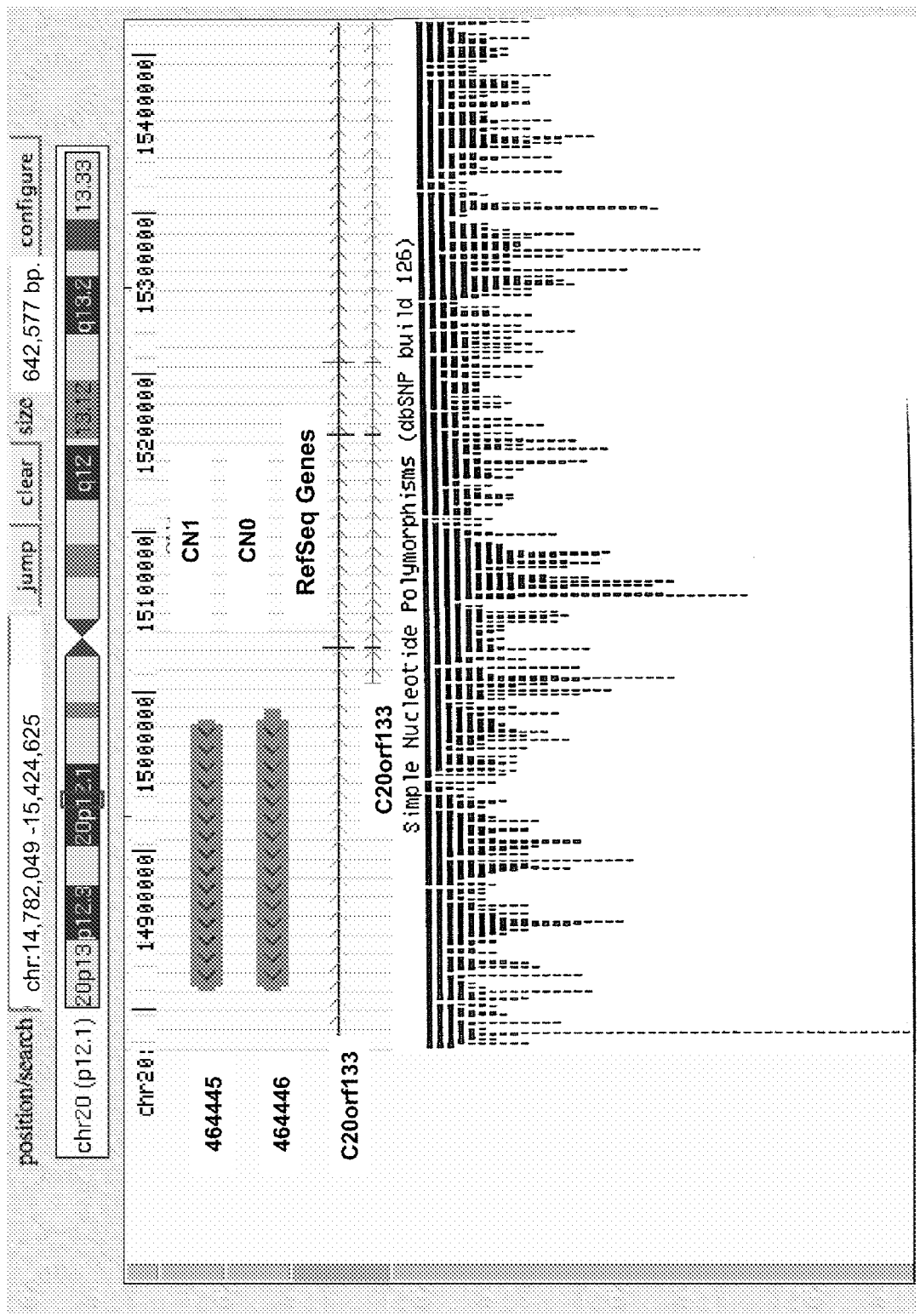
FIG. 5 is a schematic view of a common somatic copy number change on chromosome 20.

As used herein, "copy number information" means any form of information that communicates a copy number for a particular genomic locus. Specifically, copy number information could be: a numerical symbol printed on a page or displayed on a computer screen; an electrical signal; a graph; or any other means of representing the number of times a nucleotide sequence appears in a sample or in the genome of an individual cell. A non-limiting example is FIG. 5, which shows a schematic view of common somatic copy number changes on chromosome 20. The chromosomal region is indicated at the top of the figure by base position and location on the chromosome. Grey bars indicate the location of the copy number change, narrower bars indicate the approximate breakpoint location.

As used herein, two copy number profiles are "substantially similar" when they show copy number changes at one or more of the same genomic loci and said one or more genomic loci are not accounted for by germline similarities. Conversely, two copy number profiles are "substantially different" when all identities in copy number changes are accounted for by germline similarities.

Figure 1:
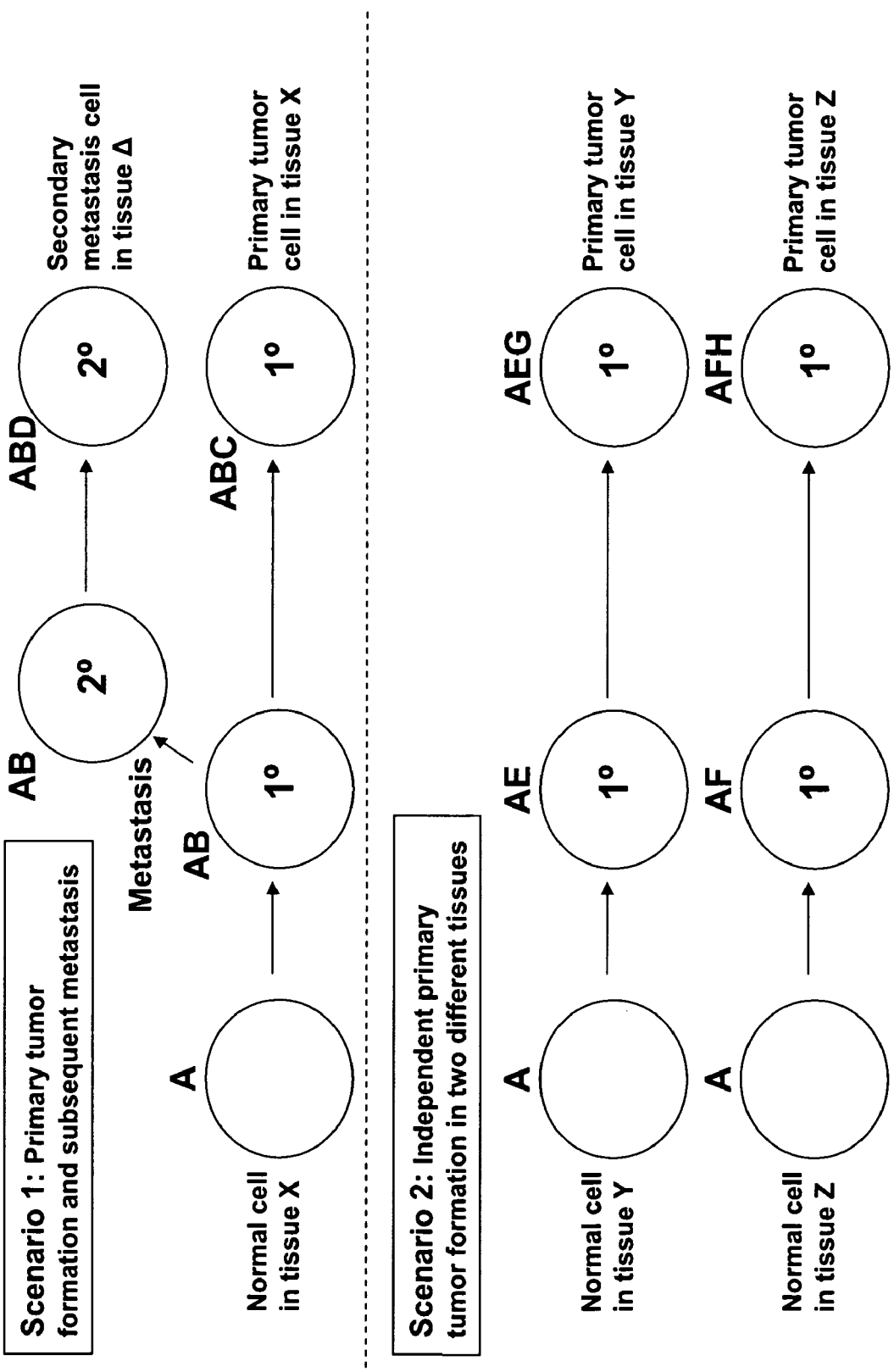
FIG. 1 is a schematic diagram of two different scenarios for the conversion of a normal cell into either one primary tumor and a subsequent secondary tumor or two independent primary tumors.

FIG. 1 illustrates what is meant by "substantially similar" and "substantially different." Scenario 1 illustrates how two tumors are generally expected to have "substantially similar" copy number profiles. More specifically, a normal cell in tissue X from an individual starts out with a particular copy number profile including particular copy numbers at certain genomic loci (A), which may be termed a germline copy number profile. This cell then mutates (B) and becomes cancerous, giving rise to a new cell (which, e.g., becomes a primary cancer) with a new copy number profile (AB). Cells having the AB genotype can then go onto to metastasize and mutate further (D), giving rise a secondary cancer with another new copy number profile (ABD). Cells in the primary tumor can continue to grow and mutate (C) independently of the secondary cancer and can be characterized as having yet another copy number profile (ABC). Thus, the primary and secondary tumors have identical copy number profiles at two loci (AB) and different profiles at the third locus (D and C). However, since the primary and secondary tumors have identical profiles at a locus (B) that is not accounted for by the germline profile, according to the present invention they are substantially similar and thus are derived from the same source. Depending on the nature of changes it is possible to determine which cancer is the primary and which cancer is the secondary, e.g., secondary cancer is typified by increased polysomy (and/or aneusomy) as compared to the primary tumor. In some embodiments, substantially similar copy number profiles will show copy number changes at 1, 2, 3, 4, 5, 6, 7, 8, 9, 10, 11, 12, 13, 14, 15, 16, 17, 18, 19, or 20 or more common genomic loci.

Scenario 2 illustrates how two tumors are generally expected to have "substantially different" copy number profiles. Normal cells in different tissues Y and Z with a common copy number profile (A) give rise independently to two different primary tumors, one characterized by a first copy number profile (AE) and the other characterized by a second copy number profile (AF). These two different tumors then go on to mutate independently giving rise to a first tumor with a copy number profile of AEG and a second tumor with a profile of AFH. The tumors in these two samples have substantially different copy number profiles because their profiles are identical only where one would expect them to be in view of the germline profile (A). In other words, the germline accounts for all similarities between the two copy number profiles.

In one embodiment, the invention provides a method for identifying independent primary cancers. According to this embodiment, genomic DNA obtained from a first suspected tumor and genomic DNA from a second suspected tumor is profiled for copy number changes in 2 or more chromosomes, at 500 Kb or better resolution. The copy number profiles of the genomic DNA from the first and second suspected tumors are compared. A substantially different copy number profile between the first tumor and second tumor indicates that they are, or are likely to be, independent primary cancers. A substantially similar DNA copy number profile between the first and second tumors indicates the cancers are related as a primary cancer and a metastasis.

In some embodiments, the two tumor samples to be analyzed are from synchronous tumors, i.e., tumor that arose or at least were discovered or treated at the same time. In other embodiments, one of the samples is from an initial tumor and the other sample(s) is from a tumor that arose later after the initial tumor was identified and/or treated. This aspect is useful for determining whether the later-arising cancer was a metastasis of the first or an independent cancer (e.g., another primary).

In one embodiment, the invention provides a method for determining the origin of genomic DNA. The method of this embodiment involves (1) obtaining genomic DNA from a first sample and second sample and (2) determining the copy number profiles for genomic DNA from the first and second samples. According to this embodiment, substantially similar copy number profiles for genomic DNA from the first and second samples indicates a common origin, e.g., they are a primary cancer and a metastatic cancer.

In one embodiment, the invention provides a method of identifying independent primary cancers and a primary/metastatic cancer. The method of this embodiment involves comparing the copy number profiles for two or more samples, each suspected of having a cancer cell or tumor tissue. The two or more samples are identified as a pair of independent primary cancer if they harbor substantially different DNA copy number profiles. The samples are identified as a primary cancer/metastatic cancer pair if they harbor substantially similar DNA copy number profiles.

In one embodiment, the invention provides a method for comparing the copy number profile of two or more tumors from a patient presenting with two or more suspected tumors. The method of this embodiment involves obtaining genomic DNA from two or more suspected tumors from a patient presenting with two or more suspected tumors and comparing their genomic DNA copy number profiles at approximately 500 kb or better resolution.

In one embodiment, the invention provides a method for comparing the copy number profile of two tumors from a patient presenting with two or more suspected tumors. The method of this embodiment involves (1) obtaining genomic DNA from a first and second sample; (2) optionally amplifying the DNA from the first and second samples; (3) contacting the amplified DNA from the first and second samples with a plurality of probes; and (4) determining the copy number profile for the genomic DNA from the first and second samples.

In one embodiment, the invention provides a method for determining the origin of genomic DNA. The method of this embodiment involves determining whether the copy number profiles of DNA from a first and second sample are substantially similar. A substantially similar DNA copy number profile for the first and second samples indicates that the samples are derived from a common precursor cell.

In one embodiment, the invention provides a method for identifying a metastasis in an individual having cancer. The method of this embodiment involves (1) obtaining, from an individual, genomic DNA from a first and second separate tumor; and (2) determining the copy number profile for genomic DNA from the first and second tumors. If the copy number profile of the genomic DNA from the first tumor and the copy number profile of the genomic DNA from the second tumor are substantially similar, this indicates that the first and second tumors are likely to be a primary and metastasis. More specifically, if the second tumor sample has additional copy number changes as compared to the first tumor, it is likely that the first tumor is the primary and the second tumor is the metastasis.

In some embodiments of the present invention, samples from two or more separate tumors are analyzed for copy number similarities and differences. In this context, two tumors are "separate tumors" if they are discrete tumor masses with some physical separation between them in the body of a patient. In a more specific aspect, the first tumor and the second tumor are obtained from anatomically distinct regions of the individual. In another aspect of this embodiment, the first and second tumors are obtained from distinct tissues of the individual. In another aspect of this embodiment, the first and second tumors are obtained from distinct organs of the individual.

In some aspects of these embodiments, the genomic DNA from the first tumor and the genomic DNA from the second tumor are obtained from two different tissues independently chosen from brain, lung, liver, spleen, kidney, lymph node, small intestine, pancreas, colon, stomach, breast, endometrial, prostate, testicle, ovary, skin, head and neck, esophagus, and bone marrow.

In some aspects of these embodiments, the genomic DNA from the first and second tumors are obtained from two different organs independently chosen from brain, lung, liver, spleen, kidney, lymph node, small intestine, pancreas, colon, stomach, breast, uterus, prostate, testicle, ovary, skin, head and neck, esophagus, and bone marrow.

In some aspects of these embodiments, the genomic DNA from the first and second tumors are obtained from two different anatomical regions independently chosen from brain, lung, liver, spleen, kidney, lymph node, small intestine, pancreas, blood cells, colon, stomach, breast, uterus, prostate, testicle, ovary, skin, head and neck, esophagus, and bone marrow.

In preferred embodiments, the copy number profile of a sample of normal, non-cancerous cells from the patient is also determined. This normal sample and its genomic DNA are preferably, though not necessarily, obtained from at least one of the same tissues from which the tumor samples are obtained. In a preferred aspect, the copy number profile of the normal sample is compared with the copy number profile of at least one of the tumor samples. In a more preferred aspect, the copy number profile of the normal sample is compared with the copy number profiles of at least two tumor samples. In such a three-or-more-way comparison the normal sample may serve as, in essence, an internal control by which any germline copy number changes shared by the tumor samples can be identified.

The two tumors to be analyzed may be taken from tumors of various types in cancers of various types. In a preferred embodiment one tumor is an ovarian tumor and the other is an endometrial tumor. In other embodiments the tumors can be chosen from tumors of the following cancers: Hodgkin's disease, non-Hodgkin's lymphoma, acute lymphocytic leukemia, chronic lymphocytic leukemia, multiple myeloma, neuroblastoma, breast carcinoma, ovarian carcinoma, lung carcinoma, Wilms' tumor, cervical carcinoma, testicular carcinoma, soft-tissue sarcoma, macroglobulinemia, bladder carcinoma, chronic granulocytic leukemia, brain carcinoma, malignant melanoma, small-cell lung carcinoma, stomach carcinoma, colon carcinoma, malignant pancreatic insulinoma, malignant carcinoid carcinoma, choriocarcinoma, mycosis fungoides, head or neck carcinoma, osteogenic sarcoma, pancreatic carcinoma, acute granulocytic leukemia, hairy cell leukemia, neuroblastoma, rhabdomyosarcoma, Kaposi's sarcoma, genitourinary carcinoma, thyroid carcinoma, esophageal carcinoma, malignant hypercalcemia, cervical hyperplasia, renal cell carcinoma, endometrial carcinoma, polycythemia vera, essential thrombocytosis, adrenal cortex carcinoma, skin cancer, ovarian carcinoma, endometrial carcinoma, prostatic carcinoma, and a cancer of unknown origin. In another preferred embodiment, at least one of the tumors is a lymphoma.

In some aspects of these embodiments, determining the copy number profile of a sample comprises determining the genotype of that sample. The term "genotype" as used herein means the nucleotide characters at a particular nucleotide variant marker (or locus) in either one allele or both alleles of a gene (or a particular chromosome region). With respect to a particular nucleotide position of a gene of interest, the nucleotide(s) at that locus or equivalent thereof in one or both alleles form the genotype of the gene at that locus. A genotype can be homozygous or heterozygous. Accordingly, "genotyping" means determining the genotype, that is, the nucleotide (s) at a particular gene locus. Genotyping can also be done by determining the amino acid variant at a particular position of a protein which can be used to deduce the corresponding nucleotide variant(s). The term "locus" as used in the context of genotyping is not identical to "genomic locus" as used in the context of copy number profiling. "Locus" in genotyping refers to a specific position or site in a gene sequence or protein. Thus, there may be one or more contiguous nucleotides in a particular gene locus, or one or more amino acids at a particular locus in a polypeptide. Moreover, "locus" may also be used to refer to a particular position in a gene where one or more nucleotides have been deleted, inserted, or inverted.

In various aspects of these embodiment, one skilled in the art will appreciate that different numbers of chromosomes and genes may be profiled at different resolutions. For example, in some embodiments, 1, 2, 3, 4, 5, 6, 7, 8, 9, 10, 11, 12, 13, 14, 15, 16, 17, 18, 19, 20, 21, or 22 or more chromosomes are profiled. In some embodiments, the resolution of the copy number profiling is about 500, 400, 300, 250, 200, 250, 200, 150, 100, 75, 50, 40, 30, 20, 10, or 5 Kb or less. As used in this context, "resolution" refers to the smallest stretch of genomic DNA (i.e., smallest "genomic locus"), on average, for which copy number changes (i.e., deletion or amplification) are detected and included in a copy number profile. Thus genomic loci according to the present invention preferably encompass stretches of genomic DNA of about 500, 400, 300, 250, 200, 250, 200, 150, 100, 75, 50, 40, 30, 20, 10, or 5 Kb or less in length.

In preferred embodiments copy number profiles are determined using single nucleotide polymorphism (SNP) microarrays. In SNP microarrays resolution is expressed as the average distance along a chromosome or genome between two SNP markers. Resolution in whole-genome SNP microarrays can be as low as 5 Kb or less. This generally means that along the entire genome, within an average stretch of 5 Kb, the microarray has probes directed to at least two different SNPs. As is known in the art, however, microarrays often have probes concentrated in areas of the genome that are of particular interest. Thus the resolution of the array within these areas may be improved to beyond 4 Kb, 3 Kb, 2 Kb or 1 Kb or better by using probes directed to SNPs staggered more tightly across these regions while omitting probes to areas of lesser interest.

In some embodiments, the copy number profile of 2 or more genes (or loci) are determined. In another aspect of this embodiment, the copy number profile of 2, 5, 10, 20, 50, 100, 200, 500, 1000, 2000, 3000, 4000, 5000, 7000, 9000, 12,000, 15,000, 20,000, 25,000, 30,000, or 40,000 or more genes (or genomic loci) are determined.

In some embodiments, the copy number profile analysis involves amplification of whole genome DNA by a whole genome amplification method. In a more specific aspect, the whole genome amplification method uses a strand displacing polymerase and random primers.

In some embodiments, the copy number profile analysis involves hybridization of DNA with a high density array. For example, a high density array can have 5,000, 10,000, 20,000, 50,000, 100,000, 200,000, 300,000, 400,000, 500,000, 600,000, 700,000, 800,000, 900,000, 1,000,000 or 3,000,000 or more different probes. Each of the different probes on the array is an oligonucleotide from about 15 to 200 bases in length from about 15 to 200, 15 to 150, 15 to 100, 15 to 75, 15 to 60, or 20 to 55 bases in length. Such high-density arrays may be used to determine copy number profiles for a certain number of chromosomes or genes or, in a preferred aspect, may be used to determine whole genome copy number profiles.

In some embodiments, one or more auxiliary genes are examined for nucleotide or genetic variants in the first and second suspected tumors. The terms "genetic variant" and "nucleotide variant" are used herein interchangeably to refer to changes or alterations to the reference human gene or cDNA sequence at a particular locus, including, but not limited to, nucleotide base deletions, insertions, inversions, and substitutions in the coding and/or non-coding regions. Deletions may be of a single nucleotide base, a portion or a region of the nucleotide sequence of the gene, or of the entire gene sequence. Insertions may be of one or more nucleotide bases. The "genetic variant" or "nucleotide variants" may occur in transcriptional regulatory regions, untranslated regions of mRNA, exons, introns, or exon/intron junctions. The "genetic variant" or "nucleotide variants" may or may not result in stop codons, frame shifts, deletions of amino acids, altered gene transcript splice forms or altered amino acid sequence. Similarly, the term "amino acid variant" is used herein to refer to an amino acid change to a reference human protein sequence resulting from "genetic variants" or "nucleotide variants" to the reference human gene encoding the reference protein. The term "amino acid variant" is intended to encompass not only single amino acid substitutions, but also amino acid deletions, insertions, and other significant changes of amino acid sequence in the reference protein.

In preferred embodiments, one or more auxiliary genes are chosen from p53, PTEN, EGFR, VEGF, bcr, abl, p16, c20orf133, TGF-β2, ctnna1, ctnnb1, KRAS, BRAF, and pik3ca. In another aspect, the one or more auxiliary genes are analyzed for variants in the first and second tumors and optionally, from a normal cell. In a specific aspect, the nucleotide sequence of a nucleic acid corresponding to the one or more auxiliary genes is analyzed. As used herein: "p53" refers to the p53 tumor suppressor having the Entrez GeneID no. 7157; "PTEN" refers to the PTEN tumor suppressor hav-ing the Entrez GeneID no. 5728; "EGFR" refers to the epidermal growth factor receptor having the Entrez GeneID no. 1956; "VEGF" refers to any of the vascular endothelial growth factors having the Entrez GeneID no. 7422, 7423, or 7424; "bcr" refers to the breakpoint cluster region having the Entrez GeneID no. 613; "abl" refers to either of the v-abl Abelson murine leukemia viral oncogenes having the Entrez GeneID no. 25 or 27; "p16" refers to the p16 tumor suppressor having the Entrez GeneID no. 1029; "c20orf133" refers to the c20orf133 tumor suppressor having the Entrez GeneID no. 140733; "TGF-β2" refers to the TGF-β2 tumor suppressor having the Entrez GeneID no. 7042; "ctnna1" refers to the ctnna1 tumor suppressor having the Entrez GeneID no. 7157; "ctnnb1" refers to the ctnnb1 tumor suppressor having the Entrez GeneID no. 1495; "KRAS" refers to the KRAS tumor suppressor having the Entrez GeneID no. 3845; "BRAF" refers to the BRAF tumor suppressor having the Entrez GeneID no. 673; and "pik3ca" refers to the pik3ca tumor suppressor having the Entrez GeneID no. 5290.

The sequences associated with each Entrez GeneID number are representative of one particular individual in the population of humans. Humans vary from one to another in their gene sequences. These variations are very minimal, sometimes occurring at a frequency of about 1 to 10 nucleotides per gene. Different forms of any particular gene exist within the human population. These different forms are called allelic variants. Allelic variants often do not change the amino acid sequence of the encoded protein; such variants are termed synonymous. Even if they do change the encoded amino acid (non-synonymous), the function of the protein is not typically affected. Such changes are evolutionarily or functionally neutral. When human gene is referred to in the present application all allelic variants are intended to be encompassed by the term. The Entrez GeneID numbers for the gene are provided merely to identify representative examples of a wild-type human sequence. The invention is not limited to this single allelic form of these genes or the proteins they encode.

In one embodiment, the invention provides a method for determining a treatment regimen. The method of this embodiment involves identifying a patient having two or more tumors. According to this embodiment, genomic DNA obtained from a first tumor and genomic DNA from a second tumor is profiled for copy number changes in one or more genomic loci, preferably at 500 Kb or better resolution. The copy number profiles of the genomic DNA from the first and second suspected tumors are compared. A substantially different copy number profile between the first tumor and second tumor indicates that they are, or are likely to be, independent primary cancers and may be treated with frontline therapy or a therapy tailored for an early stage cancer. A substantially similar DNA copy number profile between the first and second tumors indicates the cancers are related as a primary cancer and a metastasis, and may be treated as a more advanced cancer. Thus a treatment decision is made based on the results of the comparison of the copy number profiles.

Methods for DNA Copy Number Profiling

In the methods of the present invention, any method capable of providing DNA copy number profiles can be used as along as the resolution is sufficient to distinguish between genomic regions, in two different samples, having overlapping deletions or amplifications that have distinct breakpoints. The skilled artisan is aware of and capable of using a number of different platforms for assessing whole genome copy number changes at a resolution sufficient to distinguish between genomic regions, in two different samples, having overlapping deletions or amplifications that have distinct breakpoints. Some of the platforms and techniques are described in the embodiments below.

Figure 6:
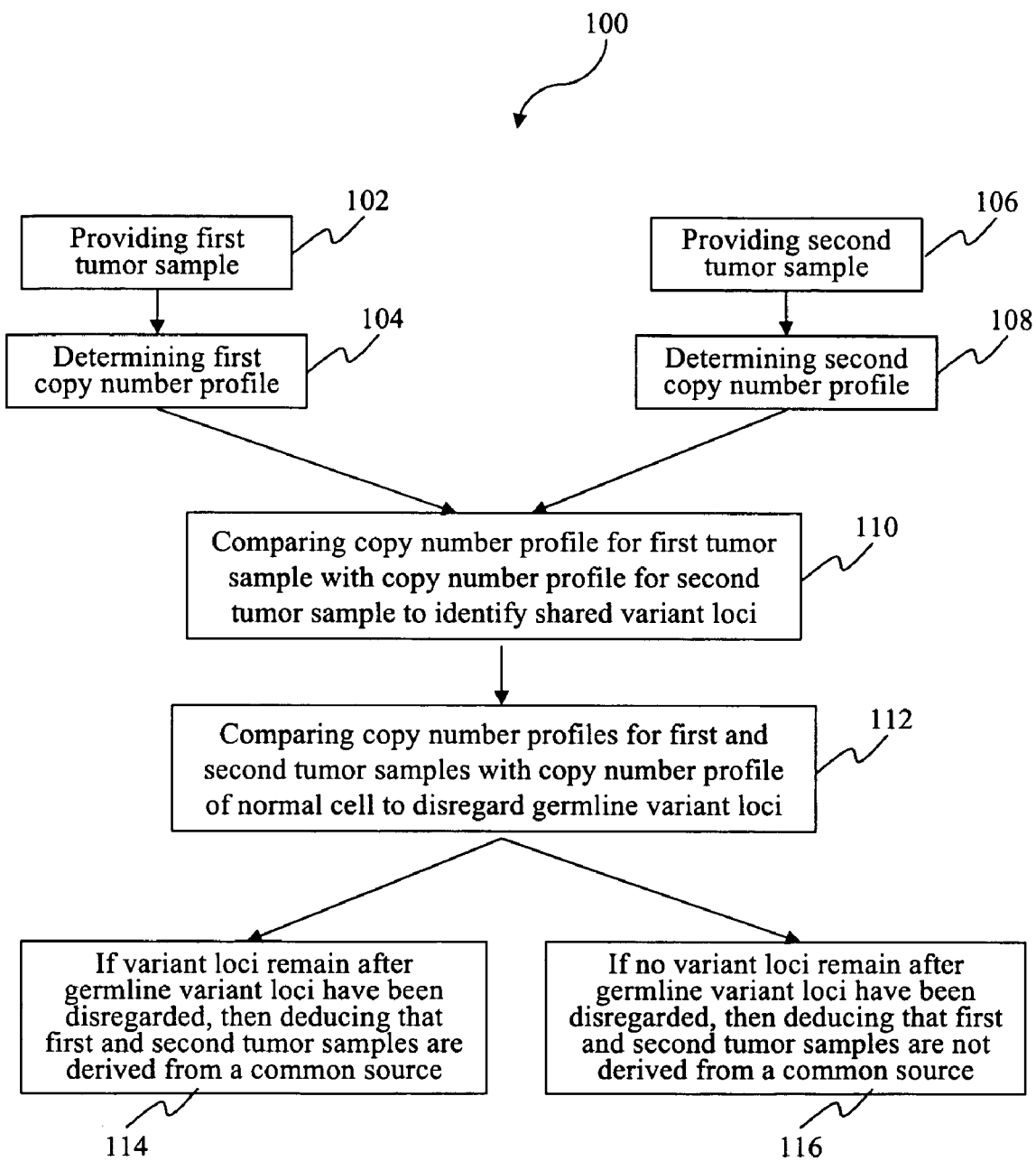
FIG. 6 is a flowchart illustrating the general steps employed in practicing some embodiments of the present invention.

In one embodiment, the present invention provides the process (100) outlined in the flowchart in FIG. 6. First, samples from two separate tumors are provided (102, 106). These samples are subjected to copy number analysis to derive a copy number profile for each (104, 108). The copy number profiles are compared to identify genomic loci at which both samples show copy numbers differing from the expected diploid number, i.e., what may be termed "variant loci" (110). The tumor sample copy number profiles are then compared with the copy number profile of a normal cell (112). This step ensures that "germline variant loci," i.e., loci where normal cells show copy number changes, are disregarded when deciding whether the two tumors are derived from a common source. If variant loci remain at which the first and second tumor both show copy number changes after germline variant loci have been disregarded, then it is deduced that the two tumors are derived from a common source (114). If no such variant loci remain after germline variant loci have been disregarded, then it is deduced that the two tumors are not derived from a common source (116).

Several of these analysis steps can be performed manually by a human subject, or by computer. In one embodiment, for example, copy number profiles can be generated using the microarray technology discussed above and in more detail below. In another embodiment the comparison amongst the copy number profiles may be done by computer in order to find only those variant loci that are not accounted for by the germline.

In many of the embodiments described below, a microarray with probes is employed to aid in determining the copy number profile for cells from a tumor. Essentially, in microarrays, a large number of different oligonucleotide probes are immobilized in an array on a substrate or carrier, e.g., a silicon chip or glass slide. Target nucleic acid sequences to be analyzed can be contacted with the immobilized oligonucleotide probes on the microchip. See Lipshutz et al., *Biotechniques*, 19:442-447 (1995); Chee et al., *Science*, 274:610-614 (1996); Kozal et al., *Nat. Med.* 2:753-759 (1996); Hacia et al., *Nat. Genet.*, 14:441-447 (1996); Saiki et al., *Proc. Natl. Acad. Sci. USA*, 86:6230-6234 (1989); Gingeras et al., *Genome Res.*, 8:435-448 (1998). Alternatively, the multiple target nucleic acid sequences to be studied are fixed onto a substrate and an array of probes is contacted with the immobilized target sequences. See Drmanac et al., *Nat. Biotechnol.*, 16:54-58 (1998). The microchip technologies combined with computerized analysis tools allow fast screening in a large scale. The adaptation of the microchip technologies to the present invention will be apparent to a person of skill in the art apprised of the present disclosure. See, e.g., U.S. Pat. No. 5,925,525 to Fodor et al; Wilgenbus et al., *J. Mol. Med.*, 77:761-786 (1999); Graber et al., *Curr. Opin. Biotechnol.*, 9:14-18 (1998); Hacia et al., *Nat. Genet.*, 14:441-447 (1996); Shoemaker et al., *Nat. Genet.*, 14:450-456 (1996); DeRisi et al., *Nat. Genet.*, 14:457-460 (1996); Chee et al., *Nat. Genet.*, 14:610-614 (1996); Lockhart et al., *Nat. Genet.*, 14:675-680 (1996); Drobyshev et al., *Gene*, 188:45-52 (1997) (all incorporated in their entirety herein by reference).

In these and other embodiments, amplification and other reactions make use of primers. The terms "primer", "probe," and "oligonucleotide" are used herein interchangeably to refer to a relatively short nucleic acid fragment or sequence. They can be DNA, RNA, or a hybrid thereof, or chemically modified analog or derivatives thereof. Typically, they are single-stranded. However, they can also be double-stranded having two complementing strands which can be separated apart by denaturation. Normally, they have a length of from about 8 nucleotides to about 200 nucleotides, preferably from about 12 nucleotides to about 100 nucleotides, and more preferably about 18 to about 50 nucleotides. They can be labeled with detectable markers or modified in any conventional manners for various molecular biological applications.

Microarrays typically comprise a plurality of oligomers (e.g., DNA or RNA polynucleotides or oligonucleotides, or other polymers), synthesized or deposited on a substrate (e.g., glass support) in an array pattern. The substrate-bound oligomers are "probes," which function to hybridize or bind with a sample material (e.g., nucleic acids prepared or obtained from the tumor samples), in hybridization experiments. The reverse situation can also be applied: the sample can be bound to the microarray substrate and the oligomer probes are in solution for the hybridization. In use, the array surface is contacted with one or more targets under conditions that promote specific, high-affinity binding of the target to one or more of the probes. In some configurations, the sample nucleic acid is labeled with a detectable label, such as a fluorescent tag, so that the hybridized sample and probes are detectable with scanning equipment. DNA array technology offers the potential of using a multitude (e.g., hundreds of thousands) of different oligonucleotides to analyze DNA copy number profiles.

Various different substances can be used as substrates in microarrays (see, e.g., in Z. Guo, et al., Nucleic Acids Res, 22, 5456-65 (1994); U. Maskos, E. M. Southern, Nucleic Acids Res, 20, 1679-84 (1992), and E. M. Southern, et al., Nucleic Acids Res, 22, 1368-73 (1994), each incorporated by reference herein). Polymer array synthesis is described extensively in the literature including in the following: WO 00/58516; U.S. Pat. Nos. 5,143,854; 5,242,974; 5,252,743; 5,324,633; 5,384,261; 5,405,783; 5,424,186; 5,451,683; 5,482,867; 5,491,074; 5,527,681; 5,550,215; 5,571,639; 5,578,832; 5,593,839; 5,599,695; 5,624,711; 5,631,734; 5,795,716; 5,831,070; 5,837,832; 5,856,101; 5,858,659; 5,936,324; 5,968,740; 5,974,164; 5,981,185; 5,981,956; 6,025,601; 6,033,860; 6,040,193; 6,090,555; 6,136,269; 6,269,846 and 6,428,752; 5,412,087; 6,147,205; 6,262,216; 6,310,189; 5,889,165; and 5,959,098 in PCT Applications Nos. PCT/US99/00730 (International Publication No. WO 99/36760) and PCT/US01/04285 (International Publication No. WO 01/58593), which are all incorporated herein by reference in their entirety for all purposes.

Arrays offer the benefit of high-throughput and high-resolution capabilities when performing copy number analysis. Recently, array-based comparative genomic hybridization (a-CGH) and other techniques have been used to discover, in key oncogenes and tumor suppressors, copy number variations between tumors known to be primary and tumors known to be a secondary metastasis. See, e.g., Buffart et al., *Cellular Oncology* (2005) 27:57-65. In this way, important mechanisms of metastasis have been elucidated.

An example of a microarray useful in the present invention is the Affymetrix® 500K SNP microarray. Whole genome copy number analysis using high density SNP chips such as this can be especially useful in determining whether two tumors in an individual are derived from a common source. The increased resolution of SNP microarrays, an average of about 5 Kb, and the huge number of probes, upwards of 1 million, make them ideal for copy number analysis according to the present invention. Nucleic acid arrays that are useful in the present invention include, but are not limited to, those that are commercially available from Affymetrix® (Santa Clara, Calif.) under the brand name Genome-Wide Human SNP Array 5.0™ or Genome-Wide Human SNP Array 6.0™.

Example arrays are shown on the website at affymetrix.com. Another microarray supplier is illumina of San Diego, Calif. with example arrays shown on their website at illumina.com.

TABLE 1

Sensitivity of the Affymetrix ® 500K microarray for copy number analysis

| Copy Number | Number of SNPs | Average Size (kb) |
|---|---|---|
| 0 | 2 | 12 |
| 1 | 6 | 36 |
| 3 | 10 | 60 |
| 4 | 6 | 36 |
| 5-6 | 4 | 24 |
| 7-11 | 3 | 18 |
| >11 | 2 | 12 |

Depending on the microarray and experiment to be performed, sample nucleic acid can be prepared in a number of ways by methods known to the skilled artisan. In some aspects of the invention, prior to or concurrent with genotyping (i.e., analysis of copy number profiles), the sample may be amplified by any number of techniques. The most common amplification procedure involves the polymerase chain reaction (PCR™). See, e.g., PCR Technology: Principles and Applications for DNA Amplification (Ed. H. A. Erlich, Freeman Press, NY, N.Y., 1992); PCR Protocols: A Guide to Methods and Applications (Eds. Innis, et al., Academic Press, San Diego, Calif., 1990); Mattila et al., Nucleic Acids Res. 19, 4967 (1991); Eckert et al., PCR Methods and Applications 1, 17 (1991); PCR (Eds. McPherson et al., IRL Press, Oxford); and U.S. Pat. Nos. 4,683,202, 4,683,195, 4,800,159 4,965,188, and 5,333,675, and each of which is incorporated herein by reference in their entireties for all purposes. In some embodiments, the sample may be amplified on the array (e.g., U.S. Pat. No. 6,300,070 which is incorporated herein by reference)

Other suitable amplification methods include the ligase chain reaction (LCR) (for example, Wu and Wallace, Genomics 4, 560 (1989), Landegren et al., Science 241, 1077 (1988) and Barringer et al. Gene 89:117 (1990)), transcription amplification (Kwoh et al., Proc. Natl. Acad. Sci. USA 86, 1173 (1989) and WO88/10315), self-sustained sequence replication (Guatelli et al., Proc. Nat. Acad. Sci. USA, 87, 1874 (1990) and WO90/06995), selective amplification of target polynucleotide sequences (U.S. Pat. No. 6,410,276), consensus sequence primed polymerase chain reaction (CP-PCR™) (U.S. Pat. No. 4,437,975), arbitrarily primed polymerase chain reaction (AP-PCR™) (U.S. Pat. Nos. 5,413,909; 5,861, 245) and nucleic acid based sequence amplification (NABSA). (See, U.S. Pat. Nos. 5,409,818, 5,554,517; and 6,063,603, each of which is incorporated herein by reference). Other amplification methods that may be used are described in, U.S. Pat. Nos. 5,242,794, 5,494,810, 4,988,617 and in U.S. Ser. No. 09/854,317, each of which are incorporated herein by reference.

Additional methods of sample preparation and techniques for reducing the complexity of a nucleic sample are described in Dong et al., Genome Research 11, 1418 (2001), in U.S. Pat. Nos. 6,361,947; 6,391,592 and U.S. Ser. Nos. 09/916,135; 09/920,491 (U.S. Patent Application Publication 20030096235), Ser. No. 09/910,292 (U.S. Patent Application Publication 20030082543), and Ser. No. 10/013,598.

Methods for conducting polynucleotide hybridization assays are well developed in the art. For example, microarrays often involve high stringency hybridization conditions. The term "high stringency hybridization conditions," when used in connection with nucleic acid hybridization, means hybridization conducted overnight at 42 degrees C. in a solution containing 50% formamide, 5×SSC (750 mM NaCl, 75 mM sodium citrate), 50 mM sodium phosphate, pH 7.6, 5×Denhardt's solution, 10% dextran sulfate, and 20 microgram/ml denatured and sheared salmon sperm DNA, with hybridization filters washed in 0.1×SSC at about 65° C. The term "moderate stringent hybridization conditions," when used in connection with nucleic acid hybridization, means hybridization conducted overnight at 37 degrees C. in a solution containing 50% formamide, 5×SSC (750 mM NaCl, 75 mM sodium citrate), 50 mM sodium phosphate, pH 7.6, 5×Denhardt's solution, 10% dextran sulfate, and 20 microgram/ml denatured and sheared salmon sperm DNA, with hybridization filters washed in 1×SSC at about 50° C. It is noted that many other hybridization methods, solutions and temperatures can be used to achieve comparable stringent hybridization conditions as will be apparent to skilled artisans.

Other hybridization assay procedures and conditions used in the methods of the invention will vary depending on the application and are selected in accordance with the general binding methods known in the art, including those referred to in: Maniatis et al. Molecular Cloning: A Laboratory Manual (2.sup.nd Ed. Cold Spring Harbor, N.Y., 1989); Berger and Kimmel Methods in Enzymology, Vol. 152, Guide to Molecular Cloning Techniques (Academic Press, Inc., San Diego, Calif., 1987); Young and Davism, P.N.A.S, 80: 1194 (1983). Methods and apparatus for carrying out repeated and controlled hybridization reactions have been described in U.S. Pat. Nos. 5,871,928; 5,874,219; 6,045,996 and 6,386,749; 6,391,623 each of which are incorporated herein by reference.

The methods of the invention may also involve signal detection of hybridization between ligands after (and/or during) hybridization. See U.S. Pat. Nos. 5,143,854, 5,578,832; 5,631,734; 5,834,758; 5,936,324; 5,981,956; 6,025,601; 6,141,096; 6,185,030; 6,201,639; 6,218,803; and 6,225,625, in U.S. Ser. No. 10/389,194 and in PCT Application PCT/US99/06097 (published as WO99/47964), each of which also is hereby incorporated by reference in its entirety for all purposes.

Methods and apparatus for signal detection and processing of intensity data are disclosed in, e.g., U.S. Pat. Nos. 5,143, 854; 5,547,839; 5,578,832; 5,631,734; 5,800,992; 5,834,758; 5,856,092; 5,902,723; 5,936,324; 5,981,956; 6,025,601; 6,090,555; 6,141,096; 6,185,030; 6,201,639; 6,218,803; and 6,225,625; in U.S. Ser. Nos. 10/389,194, 60/493,495 and in PCT Application PCT/US99/06097 (published as WO99/47964), each of which also is hereby incorporated by reference in its entirety for all purposes.

The analysis steps outlined in FIG. 6 and several of the techniques discussed above can be done manually or by computer means. For example, in order to derive a copy number profile for a tumor sample by way of a microarray, a computer means is usually employed in collecting raw signal data from the arrays as well as in analyzing and converting these raw data into an intelligible copy number profile. Furthermore, comparison amongst the copy number profiles to find variant loci not accounted for by the germline can also be performed by computer means. The analysis steps can be implemented using hardware, software or a combination thereof in one or more computer systems or other processing systems capable of effecting the steps described above within the system. The computer-based analysis function can be implemented in any suitable language and/or browsers. For example, it may be implemented with C language and preferably using object-oriented high-level programming languages such as Visual Basic, SmallTalk, C++, and the like. The application can be written to suit environments such as the Microsoft Windows™ environment including Windows™ 98, Windows™ 2000, Windows™ NT, and the like. In addition, the application can also be written for the MacIntosh™, SUN™, UNIX or LINUX environment. In addition, the functional steps can also be implemented using a universal or platform-independent programming language. Examples of such multi-platform programming languages include, but are not limited to, hypertext markup language (HTML), JAVA™, JavaScript™, Flash programming language, common gateway interface/structured query language (CGI/SQL), practical extraction report language (PERL), AppleScript™ and other system script languages, programming language/structured query language (PL/SQL), and the like. Java™- or JavaScript™-enabled browsers such as HotJava™, Microsoft™ Explorer™, or Netscape™ can be used. When active content web pages are used, they may include Java™ applets or ActiveX™ controls or other active content technologies.

A useful computer system for implementing the analysis functions described above may comprise an interface module for receiving data of the amount hybridization signal and/or identity of each SNP; and one or more computer program means for performing the analysis steps described above.

The analysis function can also be embodied in computer program products and used in the systems described above or other computer- or internet-based systems. Accordingly, another aspect of the present invention relates to a computer program product comprising a computer-usable medium having computer-readable program codes or instructions embodied thereon for enabling a processor to carry out the analysis steps described above. These computer program instructions may be loaded onto a computer or other programmable apparatus to produce a machine, such that the instructions which execute on the computer or other programmable apparatus create means for implementing the functions or steps described above. These computer program instructions may also be stored in a computer-readable memory or medium that can direct a computer or other programmable apparatus to function in a particular manner, such that the instructions stored in the computer-readable memory or medium produce an article of manufacture including instruction means which implement the analysis functions or steps. The computer program instructions may also be loaded onto a computer or other programmable apparatus to cause a series of operational steps to be performed on the computer or other programmable apparatus to produce a computer implemented process such that the instructions which execute on the computer or other programmable apparatus provide steps for implementing the functions or steps described above.

The practice of the present invention may also employ conventional biology methods, software and systems. Computer software products of the invention typically include computer readable medium having computer-executable instructions for performing the logic steps of the method of the invention. Suitable computer readable medium include floppy disk, CD-ROM/DVD/DVD-ROM, hard-disk drive, flash memory, ROM/RAM, magnetic tapes and etc. The computer executable instructions may be written in a suitable computer language or combination of several languages. Basic computational biology methods are described in, for example Setubal and Meidanis et al., Introduction to Computational Biology Methods (PWS Publishing Company, Boston, 1997); Salzberg, Searles, Kasif, (Ed.), Computational Methods in Molecular Biology, (Elsevier, Amsterdam, 1998); Rashidi and Buehler, Bioinformatics Basics: Application in Biological Science and Medicine (CRC Press, London, 2000) and Ouelette and Bzevanis Bioinformatics: A Practical Guide for Analysis of Gene and Proteins (Wiley & Sons, Inc., 2.sup.nd ed., 2001). See U.S. Pat. No. 6,420,108.

The present invention may also make use of various computer program products and software for a variety of purposes, such as probe design, management of data, analysis, and instrument operation. See U.S. Pat. Nos. 5,593,839; 5,795,716; 5,733,729; 5,974,164; 6,066,454; 6,090,555; 6,185,561; 6,188,783; 6,223,127; 6,229,911 and 6,308,170.

Additionally, the present invention may have preferred embodiments that include methods for providing genetic information over networks such as the Internet as shown in U.S. Ser. Nos. 10/197,621; 10/063,559 (U.S. Publication Number 20020183936), Ser. Nos. 10/065,856; 10/065,868; 10/328,818; 10/328,872; 10/423,403; and 60/482,389.

Methods for Analyzing Auxiliary Genes

The methods of the present invention may further comprise a step for genotyping one or more auxiliary genes to determine whether an individual has one or more nucleotide variants (or amino acid variants) in one or more of the auxiliary genes (or their encoded proteins). Genotyping one or more auxiliary genes in combination with copy number profile analysis can be particularly useful in determining whether two or more cancers from an individual are independent primary cancers or related as a primary and a metastasis, and can provide more evidence for determining therapy, diagnosis, and prognosis. For example, a common somatic point mutation (or, e.g., LOH) in the PTEN gene (or a common mutation profile in the one or more other auxiliary genes) in simultaneous tumors from an individual indicates that they are substantially similar and likely to have a common origin, e.g., one tumor is a primary and the other is a metastasis. If each tumor has a different somatic mutation in the PTEN gene, or a substantially different mutation profile in one or more of the other auxiliary genes, then the tumors are probable independent primary cancers.

The auxiliary genes of the invention can be analyzed by any method useful for determining alterations in nucleic acids or the proteins they encode. According to one embodiment, the ordinarily skilled artisan can analyze the one or more auxiliary genes for mutations including deletion mutants, insertion mutants, frameshift mutants, nonsense mutants, missense mutant, and splice mutants.

Nucleic acids used for analysis of the one or more auxiliary genes can be isolated from cells in the sample according to standard methodologies (Sambrook et al., 1989). The nucleic acid, for example, may be genomic DNA or fractionated or whole cell RNA. Where RNA is used, it may be desired to convert the RNA to a complementary DNA. In one embodiment, the RNA is whole cell RNA; in another, it is poly-A RNA. Normally, the nucleic acid is amplified.

Depending on the format of the assay for analyzing the one or more auxiliary tumors suppressor genes, the specific nucleic acid of interest is identified in the sample directly using amplification or with a second, known nucleic acid following amplification. Next, the identified product is detected. In certain applications, the detection may be performed by visual means (e.g., ethidium bromide staining of a gel); chemiluminescence, see Nelson et al., *Nucleic Acids Res.*, 24:4998-5003 (1996); radioactive scintigraphy of radiolabel or fluorescent label; or electrical or thermal impulse signals (Affymax Technology; Bellus, 1994).

Following detection, one may compare the results seen for the two or more samples from a given patient. In this way, it is possible to determine if the first and second samples harbor one or more common mutations (alterations) in the one or more auxiliary genes. Mutations in and outside the coding region of the one or more auxiliary genes may occur and can be analyzed according to the methods of the invention.

Similarly, a method for haplotyping one or more auxiliary genes is also provided. As used herein, "haplotype" is a combination of genetic (nucleotide) variants in a region of an mRNA or a genomic DNA on a chromosome found in an individual. Thus, a haplotype includes a number of genetically linked polymorphic variants which are typically inherited together as a unit. Haplotyping can be done by any methods known in the art. For example, only one copy of one or more auxiliary genes can be isolated from an individual and the nucleotide at each of the variant positions is determined. Alternatively, an allele specific PCR™ or a similar method can be used to amplify only one copy of the one or more auxiliary genes in an individual, and the SNPs at the variant positions of the present invention can be determined. The Clark method known in the art can also be employed for haplotyping. A high throughput molecular haplotyping method is also disclosed in Tost et al., Nucleic Acids Res., 30(19):e96 (2002), which is incorporated herein by reference.

For purposes of genotyping and haplotyping, both genomic DNA and mRNA/cDNA can be used, and both are herein referred to generically as "gene."

Numerous techniques for detecting nucleotide variants are known in the art and can all be used for the method of this invention. The techniques can be nucleic acid-based or protein-based. In either case, the techniques used must be sufficiently sensitive so as to accurately detect small nucleotide or amino acid variations. Very often, a probe labeled with a detectable marker is utilized. Unless otherwise specified in a particular technique described below, any suitable marker known in the art can be used, including but not limited to, radioactive isotopes, fluorescent compounds, biotin which is detectable using strepavidin, enzymes (e.g., alkaline phosphatase), substrates of an enzyme, ligands and antibodies, etc. See Jablonski et al., Nucleic Acids Res., 14:6115-6128 (1986); Nguyen et al., Biotechniques, 13:116-123 (1992); Rigby et al., J. Mol. Biol., 113:237-251 (1977).

In a nucleic acid-based detection method, a target nucleic acid sample, i.e., a sample containing genomic DNA, cDNA, and/or mRNA, corresponding to the one or more auxiliary genes generally must be obtained from the individual to be tested. Any tissue or cell sample containing the genomic DNA, mRNA, and/or cDNA (or a portion thereof) corresponding to the one or more auxiliary genes can be used. The tissue or cell samples can be analyzed directly without much processing, e.g., fluorescent in situ hybridization. Alternatively, nucleic acids including the target sequence can be extracted, purified, and/or amplified before they are subject to the various detecting procedures discussed below. Other than tissue or cell samples, cDNAs or genomic DNAs from a cDNA or genomic DNA library constructed using a tissue or cell sample obtained from the individual to be tested are also useful.

To determine the presence or absence of a particular nucleotide variant, one technique is simply sequencing the target genomic DNA or cDNA, particularly the region encompassing the nucleotide variant locus to be detected. Various sequencing techniques are generally known and widely used in the art including: the Sanger method; the Gilbert chemical method; and the newly developed pyrosequencing method. See Nordstrom et al., Biotechnol. Appl. Biochem., 31(2):107-112 (2000), Ahmadian et al., Anal. Biochem., 280:103-110 (2000) (all incorporated herein by reference).

The presence or absence of a nucleotide variant at a particular locus in the one or more auxiliary genes of an individual can also be detected using various other techniques, including: restriction fragment length polymorphism (RFLP) and AFLP methods; the single-stranded conformation polymorphism assay (SSCA), see Orita et al., Proc. Natl. Acad. Sci. USA, 86:2776-2770 (1989); denaturing gel-based techniques such as clamped denaturing gel electrophoresis (CDGE) and denaturing gradient gel electrophoresis (DGGE), see Miller et al., Biotechniques, 5:1016-24 (1999), Sheffield et al., Am. J. Hum, Genet., 49:699-706 (1991), Wartell et al., Nucleic Acids Res., 18:2699-2705 (1990); and Sheffield et al., Proc. Natl. Acad. Sci. USA, 86:232-236 (1989); double-strand conformation analysis (DSCA), see Arguello et al., Nat. Genet., 18:192-194 (1998); amplification refractory mutation system (ARMS), see e.g., European Patent No. 0,332,435, Newton et al., Nucleic Acids Res., 17:2503-2515 (1989), Fox et al., Br. J. Cancer, 77:1267-1274 (1998), Robertson et al., Eur. Respir. J., 12:477-482 (1998); mini sequencing or single nucleotide primer extension methods, see Syvanen et al., Genomics, 8:684-692 (1990), Shumaker et al., Hum. Mutat., 7:346-354 (1996), Chen et al., Genome Res., 10:549-547 (2000); oligonucleotide ligation assay (OLA), see Landergren et al., Science, 241:1077-1080 (1988), Chen et al, Genome Res., 8:549-556 (1998), Tannone et al., Cytometry, 39:131-140 (2000) (all incorporated herein by reference).

Detection of small genetic variations can also be accomplished by a variety of hybridization-based approaches, including: allele-specific oligonucleotides, see Conner et al., Proc. Natl. Acad. Sci. USA, 80:278-282 (1983), Saiki et al, Proc. Natl. Acad. Sci. USA, 86:6230-6234 (1989); mismatch detection techniques, see Cariello, Human Genetics, 42:726 (1988), Roberts et al., Nucleic Acids Res., 25:3377-3378 (1997); RNase protection assay, see Giunta et al., Diagn. Mol. Path., 5:265-270 (1996), Finkelstein et al., Genomics, 7:167-172 (1990); Kinszler et al., Science 251:1366-1370 (1991); and mutS assay, see Modrich et al., Ann. Rev. Genet., 25:229-253 (1991) (all incorporated herein by reference).

A great variety of improvements and variations have been developed in the art on the basis of the above-described basic techniques, and can all be useful in detecting mutations or nucleotide variants in the present invention. For example: fluorescence resonance energy transfer (FRET) techniques, e.g., dye-labeled oligonucleotide ligation assay, see Wolf et al., Proc. Nat. Acad. Sci. USA, 85:8790-8794 (1988), Nazarenko et al., Nucleic Acids Res., 25:2516-2521 (1997), Rychlik et al., Nucleic Acids Res., 17:8543-8551 (1989), Sharkey et al., Bio/Technology 12:506-509 (1994), Tyagi et al., Nat. Biotechnol., 14:303-308 (1996), Tyagi et al., Nat. Biotechnol., 16:49-53 (1998), Chen et al., Genome Res. 8:549-556 (1998); homo-tag assisted non-dimer system (HANDS), see Brownie et al., Nucleic Acids Res., 25:3235-3241 (1997); Dye-labeled oligonucleotide ligation assay, See Chen et al., Genome Res. 8:549-556 (1998); TaqMan, see Holland et al., Proc. Natl. Acad. Sci. USA, 88:7276-7280 (1991), Kalinina et al., Nucleic Acids Res., 25:1999-2004 (1997), Whitcombe et al., Clin. Chem., 44:918-923 (1998); base excision sequence scanning (BESS), see, e.g., Hawkins et al., Electrophoresis, 20:1171-1176 (1999) (all incorporated herein by reference).

Another useful technique that is gaining increased popularity is mass spectrometry. See Graber et al., Curr. Opin. Biotechnol., 9:14-18 (1998). For example, in the primer oligo base extension (PROBE™) method, a target nucleic acid is immobilized to a solid-phase support. A primer is annealed to the target immediately 5' upstream from the locus to be analyzed. Primer extension is carried out in the presence of a selected mixture of deoxyribonucleotides and dideoxyribonucleotides. The resulting mixture of newly extended primers is then analyzed by MALDI-TOF. See e.g., Monforte et al., *Nat. Med.*, 3:360-362 (1997).

In addition, the microchip or microarray technologies discussed above in the context of determining copy number profile are also applicable to the detection of auxiliary gene variants.

As is apparent from the above survey of the suitable detection techniques, it may or may not be necessary to amplify the target DNA, i.e., the gene, cDNA, mRNA, or a portion thereof to increase the number of target DNA molecule, depending on the detection techniques used. PCR™ amplification is well known in the art and is disclosed in U.S. Pat. Nos. 4,683,195 and 4,800,159, both which are incorporated herein by reference. For non-PCR™-based detection techniques, if necessary, the amplification can be achieved by, e.g., in vivo plasmid multiplication, or by purifying the target DNA from a large amount of tissue or cell samples. See generally, Sambrook et al., *Molecular Cloning: A Laboratory Manual*, $2^{nd}$ ed., Cold Spring Harbor Laboratory, Cold Spring Harbor, N.Y., 1989.

However, even with scarce samples, many sensitive techniques have been developed in which small genetic variations such as single-nucleotide substitutions can be detected without having to amplify the target DNA in the sample. For example: amplification of the signal as opposed to the target DNA by, e.g., employing branched DNA or dendrimers that can hybridize to the target DNA, see Detmer et al., *J. Clin. Microbiol.*, 34:901-907 (1996), Collins et al., *Nucleic Acids Res.*, 25:2979-2984 (1997), Horn et al., *Nucleic Acids Res.*, 25:4835-4841 (1997), Horn et al., *Nucleic Acids Res.*, 25:4842-4849 (1997), Nilsen et al., *J. Theor. Biol.*, 187:273-284 (1997); Invader® assay, see Cooksey et al., *Antimicrobial Agents and Chemotherapy* 44:1296-1301 (2000), Lyamichev et al., *Nat. Biotechnol.*, 17:292-296 (1999); rolling circle method, see Lizardi et al., *Nature Genetics*, 19:225-232 (1998), Clark and Pickering, *Life Science News* 6, 2000, *Amersham Pharmacia Biotech* (2000) (which are all incorporated herein by reference).

A number of other techniques that avoid amplification all together include: surface-enhanced resonance Raman scattering (SERRS), see Graham et al., *Anal. Chem.*, 69:4703-4707 (1997); fluorescence correlation spectroscopy, see Eigen et al., *Proc. Natl. Acad. Sci. USA*, 91:5740-5747 (1994); and single-molecule electrophoresis, see Castro et al., *Anal. Chem.*, 67:3181-3186 (1995) (which are all incorporated herein by reference).

Accordingly, the presence or absence of one or more auxiliary genes nucleotide variant or amino acid variant in an individual can be determined using any of the detection methods described above.

The present invention also provides a kit for genotyping the one or more auxiliary genes, i.e., determining the presence or absence of one or more of the nucleotide or amino acid variants in one or more auxiliary genes in a sample obtained from a patient. The kit may include a carrier for the various components of the kit in the form of, e.g., bag, box, tube, rack, and is optionally compartmentalized.

In one embodiment, the detection kit includes one or more oligonucleotides useful in detecting one or more of the nucleotide variants in one or more auxiliary genes. Preferably, the oligonucleotides are allele-specific. Thus, the oligonucleotides can be used in any of the mutation-detecting techniques discussed above. The oligonucleotides in this embodiment preferably have a nucleotide sequence that matches a nucleotide sequence of a variant auxiliary gene allele containing a nucleotide variant to be detected. Under most conditions, a length for the oligonucleotide of 18 to 30 may be optimum. The oligonucleotides should be designed such that they can be used in distinguishing one nucleotide variant from another at a particular locus under predetermined stringent hybridization conditions. The hybridization of an oligonucleotide with a nucleic acid and the optimization of the length and hybridization conditions should be apparent to a person of skill in the art. See generally, Sambrook et al., *Molecular Cloning: A Laboratory Manual*, $2^{nd}$ ed., Cold Spring Harbor Laboratory, Cold Spring Harbor, N.Y., 1989.

In another embodiment of this invention, the kit includes one or more oligonucleotides suitable for use in detecting techniques such as ARMS, oligonucleotide ligation assay (OLA), and the like.

The oligonucleotides in the detection kit can be labeled with any suitable detection marker including but not limited to, radioactive isotopes, fluorophores, biotin, enzymes (e.g., alkaline phosphatase), enzyme substrates, ligands and antibodies, etc. See Jablonski et al., *Nucleic Acids Res.*, 14:6115-6128 (1986); Nguyen et al., *Biotechniques*, 13:116-123 (1992); Rigby et al., *J. Mol. Biol.*, 113:237-251 (1977). Alternatively, the oligonucleotides included in the kit are not labeled, and instead, one or more markers are provided in the kit so that users may label the oligonucleotides at the time of use.

In another embodiment of the invention, the detection kit contains one or more antibodies that binds immunologically with certain proteins or polypeptides (encoded by the auxiliary genes) containing specific amino acid variants discovered in the present invention. Methods for producing and using such antibodies are known in the art.

Various other components useful in the detection techniques may also be included in the detection kit of this invention. Examples of such components include, but are not limited to, Taq polymerase, deoxyribonucleotides, dideoxyribonucleotides other primers suitable for the amplification of a target DNA sequence, RNase A, mutS protein, and the like. In addition, the detection kit preferably includes instructions on using the kit for detecting nucleotide variants in auxiliary gene sequences.

The kit may also include one or more high-density SNP microarray chips—such as the Genome-Wide Human SNP Array 5.0™ or Genome-Wide Human SNP Array 6.0™ from Affymetrix® of Santa Clara, Calif. or those available from illumina of San Diego, Calif.—useful in determining copy number profiles for tumor samples. The kit may further comprise a computer system and or a computer program product of the present invention for copy number profile comparison and analysis, which are described above.

Reporting Results

Typically, once the determination of whether two tumors share a common source and/or the presence or absence of one or more auxiliary gene nucleotide variant or an amino acid variant resulting from a nucleotide variant of the present invention is determined, physicians or genetic counselors or patients or other researchers may be informed of the result. Specifically the result can be cast in a transmittable form that can be communicated or transmitted to other researchers or physicians or genetic counselors or patients. Such a form can vary and can be tangible or intangible. The result with regard to whether two or more tumors in the individual tested share a common source can be embodied in descriptive statements, diagrams, photographs, charts, images or any other visual forms. For example, graphs showing copy number information for various genomic loci can be used in explaining the results. Diagrams showing where a variant occurs in an individual's auxiliary gene are also useful in indicating some testing results. The statements and visual forms can be recorded on a tangible media such as papers, computer readable media such as floppy disks, compact disks, etc., or on an intangible media, e.g., an electronic media in the form of email or website on internet or intranet. In addition, the result with regard to whether two or more tumors in the individual tested share a common source can also be recorded in a sound form and transmitted through any suitable media, e.g., analog or digital cable lines, fiber optic cables, etc., via telephone, facsimile, wireless mobile phone, internet phone and the like.

Thus, the information and data on a test result can be produced anywhere in the world and transmitted to a different location. For example, when a copy number or genotyping assay is conducted offshore, the information and data on a test result may be generated and cast in a transmittable form as described above. The test result in a transmittable form thus can be imported into the U.S. Accordingly, the present invention also encompasses a method for producing a transmittable form of information on the copy number profile of two or more cancer samples from an individual. The method comprises the steps of (1) determining the copy number profile for the samples according to methods of the present invention; and (2) embodying the result of the determining step in a transmittable form. The transmittable form is the product of the production method.

EXAMPLES

The following example is included to demonstrate preferred embodiments of the invention. It should be appreciated by those of skilled the art that the techniques disclosed in the example that follows represent techniques discovered by the inventor to function well in the practice of the invention, and thus can be considered to constitute preferred modes for its practice. However, those of skill in the art should, in light of the present disclosure, appreciate that many changes can be made in the specific embodiments which are disclosed and still obtain a like or similar result without departing from the concept, spirit and scope of the invention. More specifically, it will be apparent that certain agents which are both chemically and physiologically related may be substituted for the agents described herein while the same or similar results would be achieved. All such similar substitutes and modifications apparent to those skilled in the art are deemed to be within the spirit, scope and concept of the invention as defined by the appended claims.

Copy number analysis using Affymetrix 500K chips was performed on 30 samples from ovarian or endometrial tumors. 6 samples were from individuals who presented with endometrial tumors, 7 samples were from individuals who presented with ovarian tumors and 17 samples were from individuals who presented with tumors of both the ovary and endometrium. In addition, DNA from 3 normal tissue samples from 3 individuals with both ovarian and endometrial tumors was analyzed. Histological analysis of the tumors from these 3 individuals suggested that in one case the tumors were probably independent primaries; in a second there was probably an endometrial primary tumor and an ovarian metastasis; and in the third the origin of the tumors was unknown.

DNA was prepared from fresh frozen tissue samples and analyzed using Affymetrix 500K SNP microarrays according to the manufacturer's protocols. In summary, 500 ng of high quality genomic DNA is divided into two restriction digest reactions (Nsp and Sty). The products of digestion are then ligated to Affymetrix adaptors to allow for single primer amplification by PCR™. The ligated products are amplified to generate 90 µg of genomic DNA in the 200 to 1100 bp range. The PCR™ products are then purified by vacuum filtration through a clean up plate and eluted in 45 µL of elution buffer. The recovered DNA is quantified by nanodrop to determine concentration and allow for careful dilution of 90 µg of DNA into a 45 µL reaction. These products are then fragmented by DNase 1 to fragments of less than 180 bp in size. These short fragments are labeled for 4 hours and hybridized to the chips for 16 to 18 hours at 49 C. After hybridization, the chips are washed and stained on the fluidics station before entering the autoloader for scanning.

Raw intensity data generated by Affymetrix software is used as input into a computer program which analyzes the data and outputs a list of all detected copy number changes. Each SNP on a microarray generates two intensities, IA and IB, corresponding to two alleles, A and B, of the SNP. First, IA and IB are normalized by the intensities for all alleles of all SNPs present on the microarray. In order to obtain the total signal for a SNP, ISNP, adjusted for unequal allele amplification efficiency IA and IB are added. In order to obtain copy number estimation for a SNP, ISNP is normalized by the average signal of the SNP generated by running multiple non-cancerous samples with two copies of each chromosome. Estimated copy numbers for individual SNPs are combined using a Hidden Markov Model (HMM) algorithm to predict individual copy number changes. Each copy number change is defined by the copy number and by the coordinates of the start and end of the change.

Somatic copy number changes common to both ovarian and endometrial tumors from the same individual indicates a common origin and enables one to identify instances where there is a primary and metastatic tumor. The high density of the SNP chip makes it possible to detect the breakpoint of the copy number changes with a high degree of sensitivity. This is crucial for enabling accurate determination of whether copy number changes are identical between two tumors.

Example 1

Figure 2:
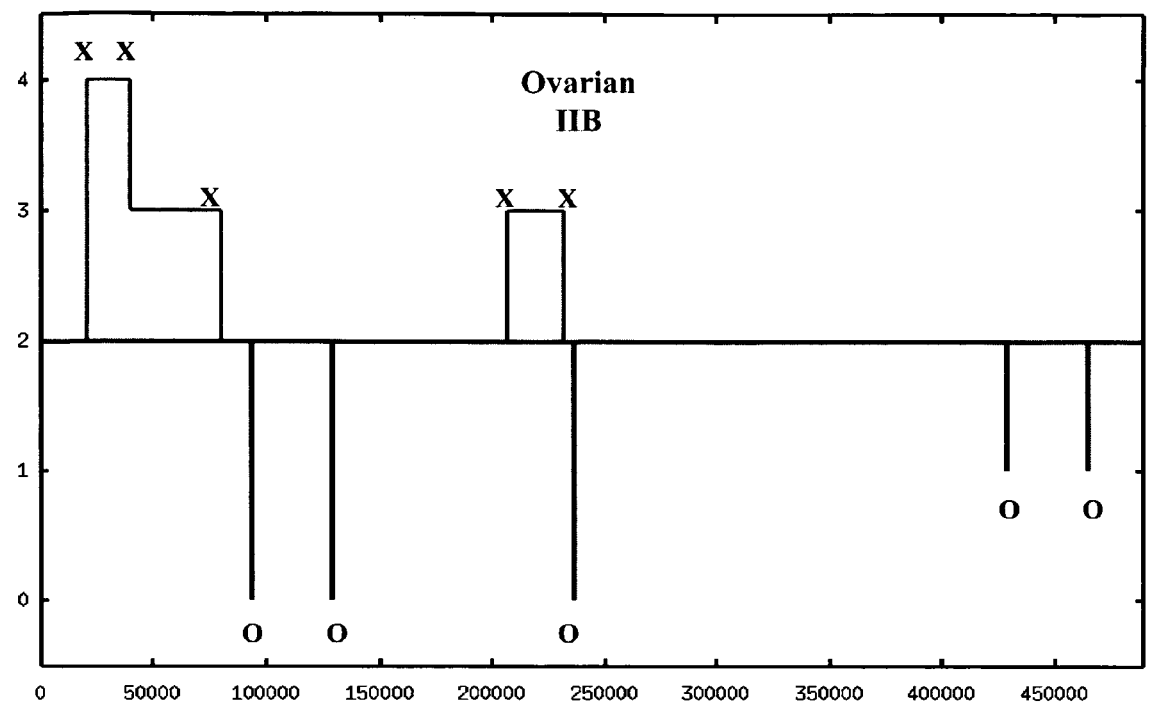
FIG. 2 is a graph showing a copy number profile confirming pathological findings suggesting independent primary ovarian and endometrial tumors.
Figure 2:
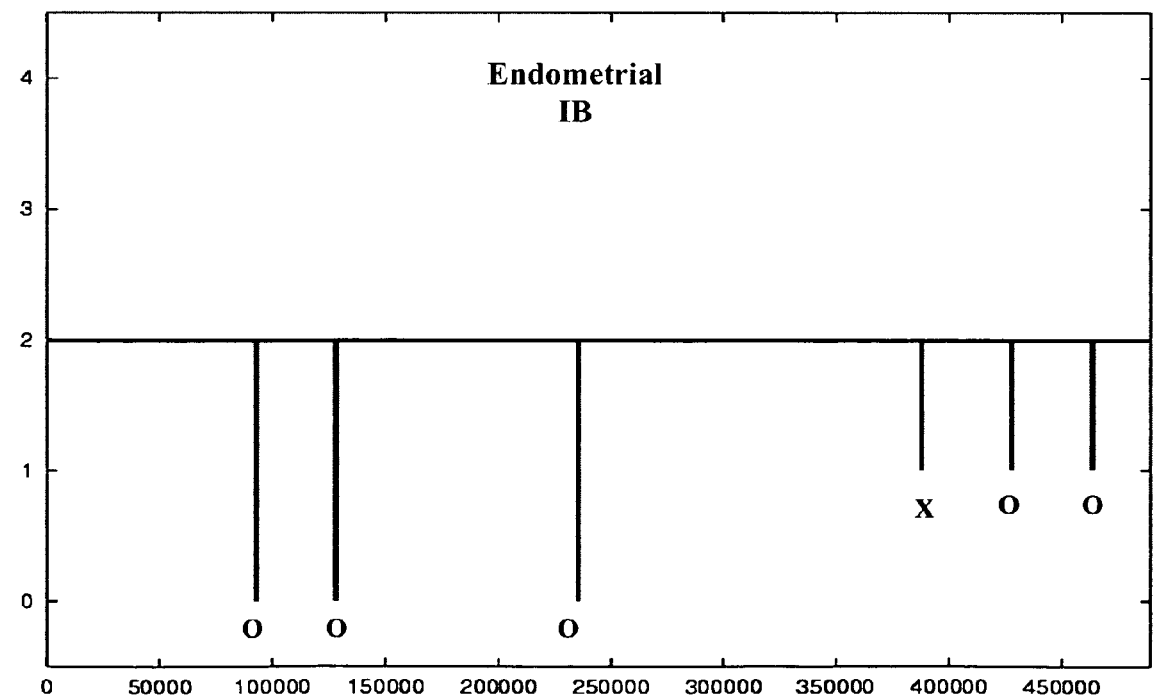

Copy Number Analysis can Determine when Simultaneous Ovarian and Endometrial Tumors are not Derived from the Same Source FIG. 2 shows the DNA copy number profile for an individual presenting with simultaneous tumors of the ovary and endometrium. Analysis of these tumors by a skilled pathologist using standard histology procedures indicated that the cancers were simultaneous primary cancers. High resolution whole genome copy number analysis showed that the two tumors harbored substantially different copy number profiles, thus confirming the pathological findings. Peaks marked with an X represent the boundaries of the somatic mutations; peaks marked with an 0 represent germline changes.

Example 2

Figure 3:
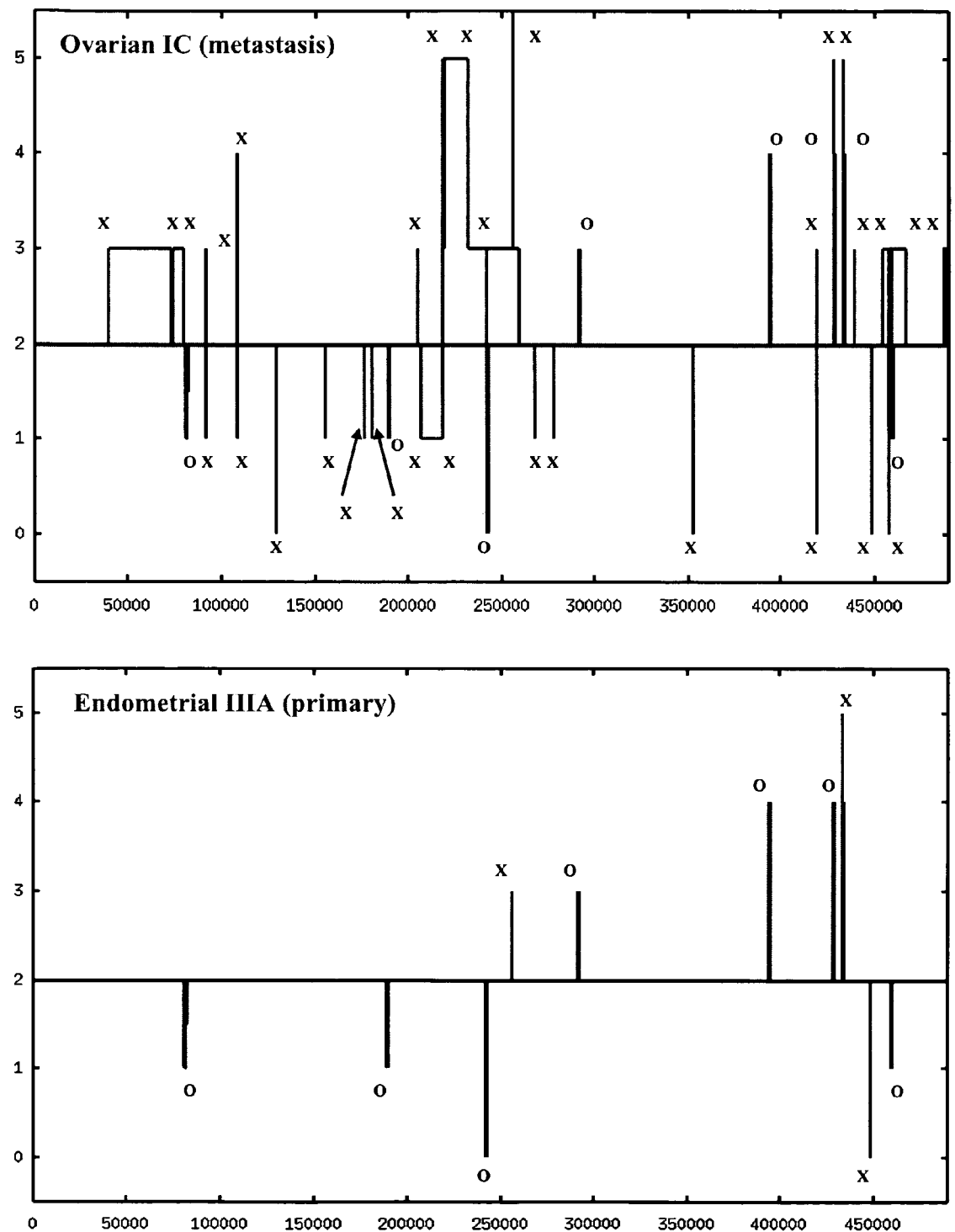
FIG. 3 is a graph showing a copy number profile confirming pathological findings suggesting primary endometrial cancer with metastasis to the ovary.

Copy Number Analysis can Confirm Histological Conclusions that Simultaneous Ovarian and Endometrial Tumors are Derived from the Same Source FIG. 3 shows the DNA copy number profiles for another individual presenting with simultaneous tumors of the ovary and endometrium. Analysis of these tumors by a skilled pathologist using standard histology procedures indicated that the cancers were a probable endometrial primary and secondary (metastasis) ovarian. Again, copy number analysis confirmed the pathological findings as high resolution whole genome copy number showed that the two tumors harbored substantially similar copy number profiles, with the secondary ovarian tumor having variations in common with primary as well as additional variations. Peaks marked with an X represent somatic mutations, peaks marked with an O represent germline changes.

Example 3

Figure 4:
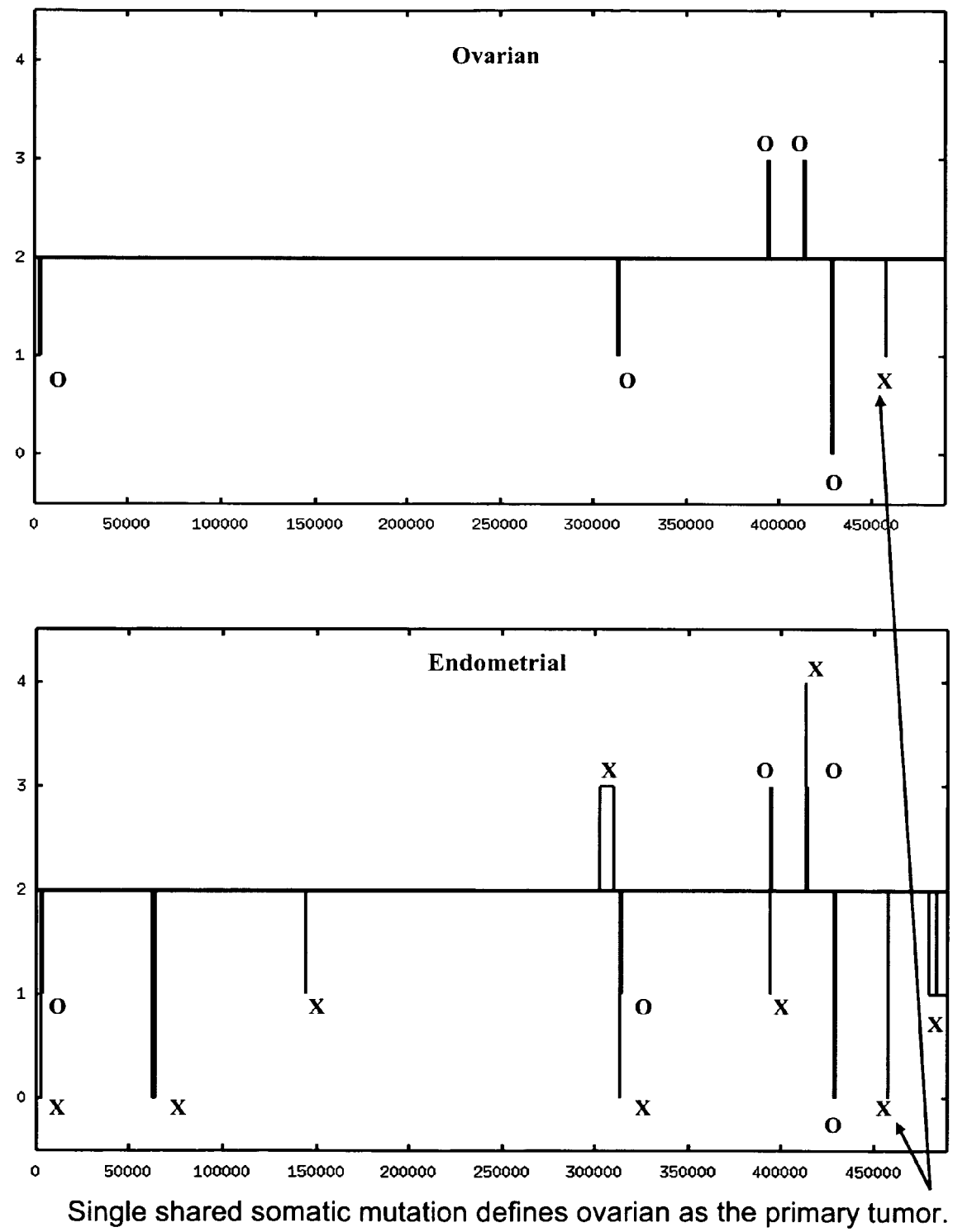
FIG. 4 is a graph showing a copy number profile indicating primary ovarian cancer with metastasis to the endometrium in a case where histological analysis was not able to determine whether these were independent or related tumors.

Copy Number Analysis can Determine that Simultaneous Ovarian and Endometrial Tumors are Derived from the Same Source in the Absence of Histological Conclusions FIG. 4 shows the DNA copy number profiles for another individual presenting with simultaneous tumors of the ovary and endometrium. Analysis of these tumors by a skilled pathologist using standard histology procedures was not able to determine the relationship cancers. Nevertheless, high resolution whole genome DNA copy number profile analysis indicated that the cancers are not independent primaries. Instead they are an ovarian tumor as a primary sharing a common somatic mutation with its endometrial metastatic secondary tumor. Additional copy number changes as well as higher copy numbers in the shared markers in the endometrial tumor identifies this as the metastasis and the ovarian as the primary tumor. Germline changes are indicated with arrows to the peaks whereas the remainder of the peaks (marked X), are somatic changes.

In each of these Figures, genomic loci where copy number differs from the expected normal diploid number of two can be considered variant loci. However, some such variant loci are found in normal cells and may be considered germline variant loci. If two tumors share variant loci other than germline variant loci, such as in FIGS. 3 & 4, then it can be deduced according to the present invention that the tumors are substantially similar and thus are derived from the same source. If two tumors share no variant loci other than germline variant loci, such as in FIG. 2, then it can be deduced according to the present invention that the tumors are substantially different and thus are not derived from the same source.

This example shows the power of the present invention in discerning between primary and metastatic tumors in just one of numerous possible tissue pairs. In fact, the present invention can be generally applied to help in identifying and staging tumors in any two or more tissues.

All publications and patent applications mentioned in the specification are indicative of the level of those skilled in the art to which this invention pertains. All publications and patent applications are herein incorporated by reference to the same extent as if each individual publication or patent application was specifically and individually indicated to be incorporated by reference. The mere mentioning of the publications and patent applications does not necessarily constitute an admission that they are prior art to the instant application.

Although the foregoing invention has been described in some detail by way of illustration and example for purposes of clarity of understanding, it will be obvious that certain changes and modifications may be practiced within the scope of the appended claims.

What is claimed is:

1. A method of determining whether two separate tumor samples are derived from the same source, comprising:

providing a first copy number profile from a first tumor sample obtained from a patient, said first copy number profile comprising copy number information for a plurality of genomic loci;

providing a second copy number profile from a second tumor sample obtained from said patient, said second copy number profile comprising copy number information for said plurality of genomic loci;

comparing said first copy number profile and said second copy number profile;

wherein if said first copy number profile is substantially similar to said second copy number profile, it indicates said first tumor sample and said second tumor sample are from the same source; and wherein if said first copy number profile is substantially different from said second copy number profile, it indicates said first tumor sample and said second tumor sample are from different sources.

2. The method of claim 1 wherein said first tumor sample is an ovarian tumor sample and wherein said second tumor sample is an endometrial tumor sample.

3. A method of determining whether two separate tumor samples are derived from the same source, comprising:

providing a first copy number profile from a first tumor sample obtained from a patient, said first copy number profile comprising copy number information for a plurality of genomic loci at a resolution of at least 500 Kb;

providing a second copy number profile from a second tumor sample obtained from said patient, said second copy number profile comprising copy number information for said plurality of genomic loci at a resolution of at least 500 Kb;

comparing said first copy number profile and said second copy number profile;

wherein if said first copy number profile is substantially similar to said second copy number profile, it indicates said first tumor sample and said second tumor sample are from the same source; and wherein if said first copy number profile is substantially different from said second copy number profile, it indicates said first tumor sample and said second tumor sample are from different sources.

4. A method of determining whether two separate tumor samples are derived from the same source, comprising:

providing a first copy number profile from a first tumor sample obtained from a patient, said first copy number profile comprising copy number information for a plurality of genomic loci;

providing a second copy number profile from a second tumor sample obtained from said patient, said second copy number profile comprising copy number information for said plurality of genomic loci;

providing a comparison between said first copy number profile and said second copy number profile;

wherein if said first copy number profile is substantially similar to said second copy number profile, it indicates said first tumor sample and said second tumor sample are from the same source; and wherein if said first copy number profile is substantially different from said second copy number profile, it indicates said first tumor sample and said second tumor sample are from different sources.

5. A method of determining whether two separate tumor samples are derived from the same source, comprising:

providing a first copy number profile from a first tumor sample obtained from a patient, said first copy number profile comprising copy number information for a plurality of genomic loci;

providing a second copy number profile from a second tumor sample obtained from said patient, said second copy number profile comprising copy number information for said plurality of genomic loci;

comparing said first copy number profile and said second copy number profile;

communicating the results of said comparing step to a third party;

wherein if said first copy number profile is substantially similar to said second copy number profile, said third party concludes said first tumor sample and said second tumor sample are from the same source; and wherein if said first copy number profile is substantially different from said second copy number profile, said third party concludes said first tumor sample and said second tumor sample are from different sources.

6. A method of determining whether two separate tumor samples are derived from the same source, comprising:

determining a first copy number profile from a first tumor sample obtained from a patient by measuring copy number information for a plurality of genomic loci;

determining a second copy number profile from a second tumor sample obtained from said patient by measuring copy number information for said plurality of genomic loci;

comparing said first copy number profile and said second copy number profile;

wherein if said first copy number profile is substantially similar to said second copy number profile, it indicates said first tumor sample and said second tumor sample are from the same source; and wherein if said first copy number profile is substantially different from said second copy number profile, it indicates said first tumor sample and said second tumor sample are from different sources.

7. The method of claim 6, further comprising displaying said first and second copy number profiles on an electronic display.

* * * * *